US012810743B1

(12) United States Patent
Robb et al.

(10) Patent No.: US 12,810,743 B1
(45) Date of Patent: Nov. 24, 2026

(54) METHODS AND APPARATUS FOR DYNAMIC GENERATION OF AUDIO VISUAL CONTENT BASED ON USER-SPECIFIC DATA

(71) Applicant: Stride, Inc., Reston, VA (US)

(72) Inventors: P Bradley Robb, Cartersville, VA (US); Zoey Rawlins, Arlington, VA (US); Denis Kulikov, Los Angeles, CA (US); Jae Yeun Moon, Lawrenceville, GA (US); Kiara Farias, Miami, FL (US); Selvedin Alic, Eagan, MN (US); Jonathan Bryan Charnock, Glen Allen, VA (US); Jose Rafael Almonte, Brooklyn, NY (US); Blake Joshua Hamm, Ogden, UT (US); Matthew Michael Fialkowski, Lehi, UT (US)

(73) Assignee: Stride, Inc., Reston, VA (US)

(*) Notice: Subject to any disclaimer, the term of this patent is extended or adjusted under 35 U.S.C. 154(b) by 9 days.

(21) Appl. No.: 19/425,323

(22) Filed: Dec. 18, 2025

(51) Int. Cl.
*G09B 7/08* (2006.01)
*A61B 5/16* (2006.01)
*G06F 40/40* (2020.01)
*H04L 9/06* (2006.01)

(52) U.S. Cl.
CPC ................ *G09B 7/08* (2013.01); *A61B 5/163* (2017.08); *A61B 5/168* (2013.01); *G06F 40/40* (2020.01); *H04L 9/06* (2013.01); *H04L 9/0643* (2013.01)

(58) Field of Classification Search
CPC ........... G09B 7/08; A61B 5/163; A61B 5/168; G06F 40/40; H04L 9/06; H04L 9/0643
See application file for complete search history.

(56) References Cited

U.S. PATENT DOCUMENTS

| | | | |
|---|---|---|---|
| 11,898,865 | B1 | 2/2024 | Bhavsar et al. |
| 12,227,154 | B2 | 2/2025 | Beier et al. |
| 12,353,444 | B1 | 7/2025 | Khosla et al. |
| 2009/0202969 | A1 | 8/2009 | Beauchamp et al. |
| 2018/0218268 | A1 | 8/2018 | Kozloski et al. |
| 2018/0232247 | A1 | 8/2018 | Potter et al. |

(Continued)

OTHER PUBLICATIONS

Hernandez-De-Menendez, M. et al., "Biometric applications in education," International Journal on Interactive Design and Manufacturing (IJIDeM), (Jul. 28, 2021), 15(2-3):365-380.

(Continued)

*Primary Examiner* — Kesha Frisby
(74) *Attorney, Agent, or Firm* — COOLEY LLP

(57) ABSTRACT

A first interaction stored in a first set of containers is sent to a remote compute device associated with a user. A second interaction based on the first interaction is received from the remote compute device. The second interaction and a conversation history associated with the second interaction are analyzed using a first stateless agent to generate a first interaction package using a second set of containers. The second interaction and the conversation history are analyzed using a second stateless agent different from the first stateless agent to generate a second interaction package that is different from the first interaction package and using the second set of containers. The first interaction package and the second interaction package are sent to a model configured to generate a third interaction responding to the second interaction based on the first interaction package and the second interaction package.

21 Claims, 7 Drawing Sheets

400

(56) References Cited

U.S. PATENT DOCUMENTS

| | | | |
|---|---|---|---|
| 2019/0197415 | A1 | 6/2019 | Bulut et al. |
| 2019/0362138 | A1 | 11/2019 | Shkedy et al. |
| 2021/0174239 | A1 | 6/2021 | Liao et al. |
| 2021/0264520 | A1 | 8/2021 | Cummings |
| 2023/0185820 | A1 | 6/2023 | Benoit |

OTHER PUBLICATIONS

Rudra, S., “How Can Biometrics be Used in Higher Education Classrooms?” EdTech Magazine, (Nov. 14, 2023). Retrieved on Dec. 30, 2025 from the Internet at URL: https://edtechmagazine.com/higher/article/2023/11/how-can-biometrics-be-used-higher-education-classrooms; 2 pages.

METHODS AND APPARATUS FOR DYNAMIC GENERATION OF AUDIO VISUAL CONTENT BASED ON USER-SPECIFIC DATA

FIELD

One or more embodiments related to methods and apparatus for dynamic generation of audio visual content based on user-specific data.

BACKGROUND

Some known systems for generating interactive content do not adapt dynamically to a user's cognitive state. These known systems lack mechanisms to incorporate physiological or behavioral indicators such as past user experience and/or biometric signals into the generation process. This limitation results in rigid interaction flows that do not account for user distraction, stress, or engagement levels during a session. Furthermore, some known systems use models that restrict scalability and increase latency when generating personalized outputs. These challenges underscore the desire for a system that can (i) process multimodal data streams-including past user experience and/or biometric inputs securely and efficiently, (ii) employ stateless, containerized agents for parallelized analysis, and (iii) orchestrate large language models to synthesize adaptive responses in real time.

SUMMARY

In an embodiment, a first interaction stored in a first set of containers is sent to a remote compute device. A second interaction based on the first interaction and data associated with the user are received from the remote compute device. The second interaction, a conversation history associated with the second interaction, and the data associated with the user are analyzed, using a first stateless agent, to generate a first interaction package using a second set of containers different than the first set of containers. The conversation history is stored in the first set of containers. The second interaction, the conversation history, and the data associated with the user are analyzed, using a second stateless agent different from the first stateless agent, to generate a second interaction package that is different from the first interaction package and using the second set of containers. The first interaction package includes a first prompt not included in the second interaction package and the second interaction package includes a second prompt not included in the first interaction package. The first interaction package and the second interaction package are sent to a large language model configured to generate a third interaction responding to the second interaction based on the first interaction package and the second interaction package. A representation of the third interaction is sent to the remote compute device that is personalized to the user.

In an embodiment, a first interaction is sent via a processor of a first compute device to a second compute device. The second compute device is associated with a user. Generating the first interaction includes extracting a reference from source material. The reference is associated with contextual information within the source material. Generating the first interaction further includes defining a template based on the reference and the contextual information. Generating the first interaction further includes aligning the template using a first large language model and a graph database to generate an aligned template. The first large language model is trained using reinforcement learning. Generating the first interaction further includes inputting the aligned template into a machine learning model configured to generate the first interaction. A second interaction based on the first interaction and biometric data associated with the user are received via the processor and from the second compute device. The second interaction, a conversation history associated with the second interaction, and the biometric data are analyzed via the processor and using a stateless agent to generate an interaction package. The interaction package is sent, via the processor, to a second large language model configured to generate a third interaction responding to the second interaction. A representation of the third interaction is sent to the second compute device.

In an embodiment, a first interaction stored in a first set of containers is sent to a remote compute device associated with a user. A second interaction based on the first interaction is received from the remote compute device. The second interaction and a conversation history associated with the second interaction are analyzed using a first stateless agent to generate a first interaction package using a second set of containers. The conversation history is stored in the first set of containers. The second interaction and the conversation history are analyzed using a second stateless agent different from the first stateless agent to generate a second interaction package that is different from the first interaction package and using the second set of containers. The first interaction package and the second interaction package are sent to a model configured to generate a third interaction responding to the second interaction based on the first interaction package and the second interaction package. A representation of the third interaction is sent to the remote compute device.

DETAILED DESCRIPTION

Some implementations relate to generating personalized content using user input and data associated with a user (e.g., biometric data, contextual data, history, etc.). A server sends an initial interaction, like a question, to a user device. The user device returns a response along with data associated with the user (e.g., biometric data from sensors). The server analyzes this information using multiple stateless agents, which run in a containerized environment. These agents generate different interaction packages, and the packages are processed by a large language model (LLM) to define a final response tailored to the user's current state, such as engagement or distraction level.

In some implementations, an "interaction" refers to data that is to be shared from a first compute device to a second compute device. For example, a variant sent from a server-side compute device to a user compute device can be an interaction, a response to the variant sent from the user compute device to the server-side compute device can be another interaction, and an output responsive to the response sent from the server-side compute device to the user compute device can be another interaction. Examples of interactions that will be discussed later in the context of FIG. 1 include variant 106, response 108, and output 124.

Figure 1:
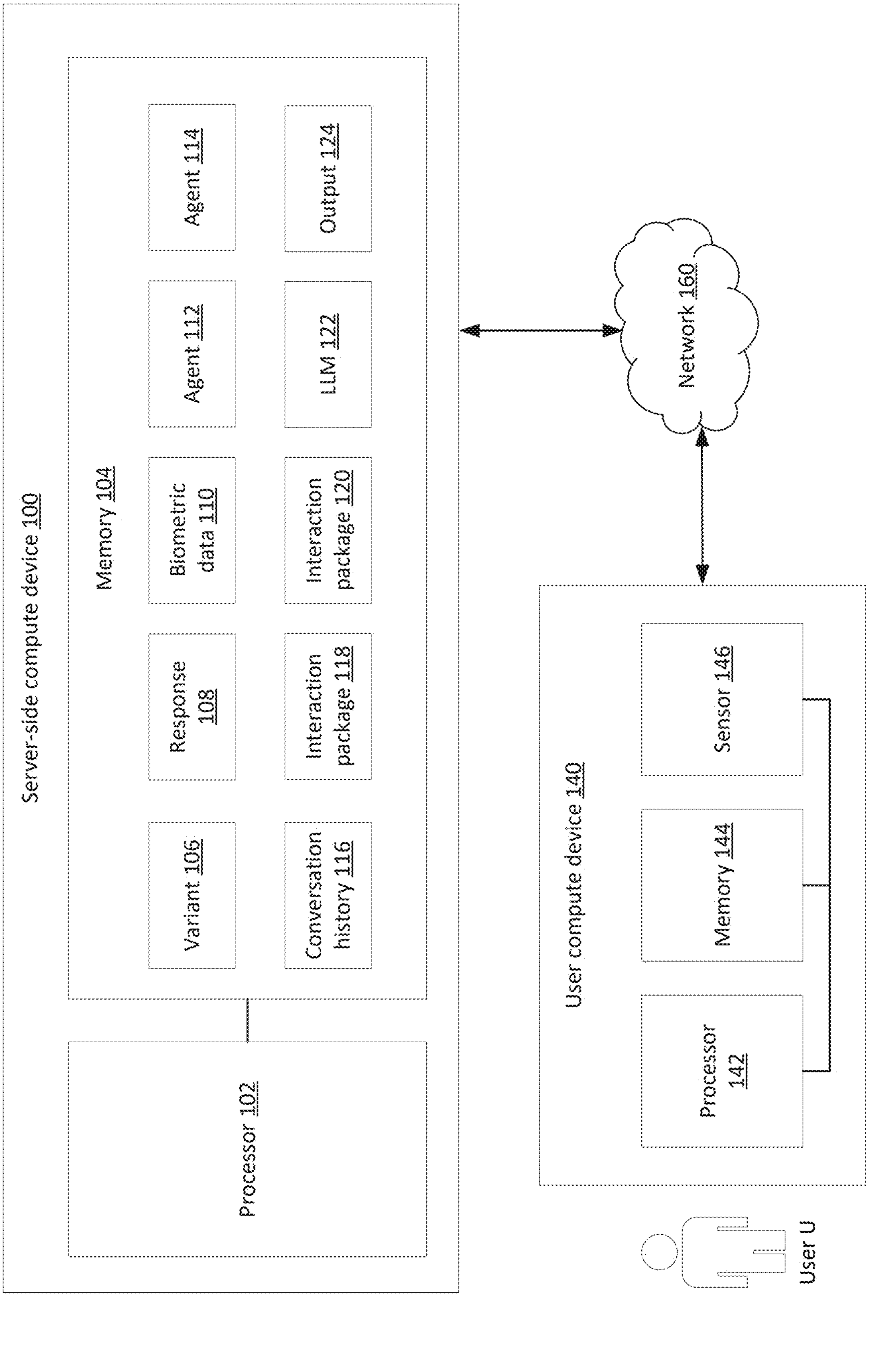
FIG. 1 illustrates a system block diagram that includes a server-side compute device and user compute device, according to an embodiment.

FIG. 1 illustrates a system block diagram that includes a server-side compute device and user compute device, according to an embodiment. FIG. 1 includes server-side compute device 100 and user compute device 140, communicably coupled to each other via network 160.

Network 160 can be any suitable communications network for transferring data, operating over public and/or private networks. For example, a network can include a private network, a Virtual Private Network (VPN), a Multiprotocol Label Switching (MPLS) circuit, the Internet, an intranet, a local area network (LAN), a wide area network (WAN), a metropolitan area network (MAN), a worldwide interoperability for microwave access network (WiMAX®), an optical fiber (or fiber optic)-based network, a Bluetooth® network, a virtual network, and/or any combination thereof. In some instances, network 160 can be a wireless network such as, for example, a Wi-Fi or wireless local area network ("WLAN"), a wireless wide area network ("WWAN"), and/or a cellular network. In other instances, network 160 can be a wired network such as, for example, an Ethernet network, a digital subscription line ("DSL") network, a broadband network, and/or a fiber-optic network. In some instances, network 160 can be a combination of a wireless network(s) and a wired network(s). In some instances, network 160 can use Application Programming Interfaces (APIs) and/or data interchange formats (e.g., Representational State Transfer (REST), JavaScript Object Notation (JSON), Extensible Markup Language (XML), Simple Object Access Protocol (SOAP), and/or Java Message Service (JMS)). The communications sent via network 160 can be encrypted or unencrypted. In some instances, network 160 can include multiple networks or subnetworks operatively coupled to one another by, for example, network bridges, routers, switches, gateways and/or the like.

Server-side compute device 100 and user compute device 140 can each be any type of compute device, such as a server, desktop, laptop, tablet, phone, and/or the like. In some implementations, server-side compute device 100 is a server and user compute device 140 is a desktop, laptop, tablet, or phone. User compute device 140 can be associated with (e.g., used by, accessible by, logged in using an account in the name of, etc.) user U. In some implementations, user U is a student.

Server-side compute device 100 includes processor 102 operatively coupled to memory 104 (e.g., via a system bus). User compute device 140 includes processor 142, memory 144, and sensor 146, each operatively coupled to one another (e.g., via a system bus).

Processor 102 and/or 142 can be, for example, a hardware-based integrated circuit (IC) or any other suitable processing device configured to run or execute a set of instructions or a set of codes. For example, processor 102 and/or 142 can include a general purpose processor, a central processing unit (CPU), an accelerated processing unit (APU), an application specific integrated circuit (ASIC), a field programmable gate array (FPGA), a programmable logic array (PLA), a complex programmable logic device (CPLD), a programmable logic controller (PLC), a graphics processing unit (GPU), a neural network processor (NNP), and/or the like.

Processor 102 can be operatively coupled to memory 104 through a system bus (e.g., address bus, data bus, and/or control bus). Processor 142 can be operatively coupled to memory 144 and sensor 146 through a system bus (for example, address bus, data bus, and/or control bus). Memory 104 and/or 144 can store electronic information. The term memory can refer to various types of processor-readable media such as, for example, random access memory (RAM), read-only memory (ROM), non-volatile random access memory (NVRAM), programmable read-only memory (PROM), erasable programmable read only memory (EPROM), electrically erasable PROM (EEPROM), flash memory, magnetic or optical data storage, registers, etc.

Sensor 146 can include one or more sensors configured to capture data associated with user U. In some implementations, sensor 146 includes a sensor(s) configured to capture biometric data associated with user U, such as a camera, motion sensor, thermal sensor, light sensor, and/or the like. Further, although not explicitly shown in FIG. 1, sensors can be coupled to or on user U, such as a heart rate monitor, temperature sensor, glucose sensor, and/or the like. Such sensors can be configured to send their collected sensor data to user compute device 140 and/or server-side compute device 100 (e.g., via network 160).

Memory 104 of server-side compute device 100 can include variant 106. In some implementations, variant 106 represents a structured item of source material—such as a question, exercise, or scenario—used to engage user U in a learning or assessment context. Said similarly, variant 106 can represent a content element or problem instance that serves as the basis for generating an interaction (e.g., response 108). For example, in some implementations, variant 106 can be an academic problem, such as a math equation, a science question, a writing prompt, or a reading comprehension prompt. In some implementations, variant 106 includes multimedia elements like diagrams or images associated with the problem.

In some implementations, an electronic signal representing variant 106 is sent from server-side computer device 100 (e.g., using processor 102) to user compute device 140 via network 160. In response to receiving the electronic signal representing variant 106, user compute device 140 (e.g., using processor 142) can output a representation of variant 106 (e.g., to user U). For example, user compute device 140 can visually display a representation of variant 106 using a display (not shown in FIG. 1) included in user compute device 140, output audio representing variant 106 using speakers (not shown in FIG. 1), and/or the like.

Memory 104 of server-side compute device 100 can also include response 108. In some implementations, response 108 represents input or feedback provided in relation to or response to variant 106. In some implementations, response 108 represents user-generated content (e.g., generated by user U at user compute device 140) that attempts to address or react to variant 106, such as a proposed answer, a clarification question, and/or an explanatory comment. For example, if variant 106 is a math problem, response 108 can be user U's proposed solution; if variant 106 is a science question, response 108 could include a hypothesis or a request for additional context.

In some implementations, an electronic signal representing response 108 is received at server-side compute device 100 from user compute device 140 via network 160 after user U provides response 108 using an input mechanism at user compute device 140 (e.g., a keyboard, mouse, touchscreen, or microphone). For example, in response to user compute device 140 displaying variant 106, user U can provide response 108 to variant 106 at user compute device 140; thereafter, response 108 can be sent from user compute device 140 (e.g., using processor 142) to server-side compute device 100 (e.g., received using processor 102).

In some implementations, memory 104 of server-side compute device 100 can also include biometric data 110. Biometric data can be captured by sensor 146 and/or a sensor(s) coupled to user U. Biometric data 110 can represent physiological or behavioral indicators associated with user U that are captured before, during, or after user U provides response 108 to variant 106. Biometric data 110 can encompass one or more attributes, each collected by one or more sensors from sensors 146 and/or a sensor(s) coupled to user U, and be used (e.g., by a neural network trained using biometric data as input learning data and associated states as target learning data) to evaluate aspects of the user U's state in the context of learning or interaction. In some implementations, server-side compute device 100 is configured to determine a state(s) of user Ut based on biometric data 110. Said similarly, biometric data 110 can be analyzed to determine user U's state such as distraction level, stress, engagement, or readiness, enabling the system to adapt subsequent variants or responses to optimize learning outcomes. Examples of biometric data 110 and associated states include: eye movement and gaze tracking, captured by camera-based eye trackers or infrared sensors, which can be used to assess attention span or detect signs of distraction; facial expressions and micro-expressions, detected by high-resolution cameras, which can indicate frustration, confusion, or engagement; heart rate and heart rate variability, measured by wearables or optical sensors, which can infer stress levels or cognitive effort; skin conductance, captured by galvanic skin response sensors, which can reveal arousal or anxiety during problem-solving; voice tone and speech patterns, analyzed via microphones to identify confidence or hesitation; posture and body movement, tracked by depth cameras or accelerometers to detect restlessness; pupil dilation, measured by eye-tracking cameras to gauge cognitive load; thermal cameras or wearable thermometers that can monitor temperature and perspiration to infer discomfort or stress; glucose monitors and drowsiness detection systems that can identify hunger or fatigue; behavioral patterns linked to attention-deficit/hyperactivity disorder (ADHD) or similar conditions which can be detected through a combination of eye trackers, motion sensors to detect fidgeting or repeated leaving/arriving; and/or the like.

Memory 104 of server-side compute device 100 can also include conversation history 116. In some implementations, conversation history 116 represents records of prior interactions that provide contextual information for generating personalized responses. In some implementations, conversation history 116 can include a sequence of one or more exchanges between user compute device 140 and user U during a current session (e.g., a single lesson, a tutoring session, a block of interactions occurring within the same login period, such as answering multiple questions in one sitting or completing a set of related exercises without logging out), enabling relevance in ongoing dialogue. In some implementations, conversation history 116 can include older chats with the same user (e.g., user U) from previous sessions, allowing longer-term personalization to be maintained based on past learning patterns or preferences. Conversation history 116 can be stored as raw text, structured data, or embedded representations. In some implementations, conversation history 116 does not include personally identifiable information and/or the personally identifiable information is masked. For example, a version of conversation history 116 that includes personally identifiable information can be modified (e.g., by processor 102 and/or 142) to remove and/or mask the personally identifiable information and generate conversation history 116. Such implementations can increase privacy and remove unwanted bias from the models using the conversation history 116.

Memory 104 of server-side compute device 100 can also include agent 112, agent 114, interaction package 118, and interaction package 120. Agents 112 and 114 are each implemented as machine learning models configured to operate as stateless agents. Interaction packages 118 and 120 can each include one or more prompts, and represent a proposed response to response 108. In some implementations, agents 112 and 114 each receive inputs that can include conversation history 116, response 108, and/or biometric data 110. Based on these inputs, each agent 112 and 114 independently generates an interaction package 118 and 120, respectively, which represents a proposed response to the user's prior input-response 108. For example, an interaction package can provide feedback on whether the user's answer is correct, suggest corrections, or respond to a clarification question or comment. In some implementations, agent 112 and/or 114 generates interaction package 118 and/or 120 without using biometric data 110.

Agent 112 and 114 can be configured to generate different types (e.g., teaching styles) of interaction packages responsive to response 108. Said differently, interaction package 118 can be different than interaction package 120 (e.g., interaction package 118 includes a prompt-such as a question, answer, or comment—not included in interaction package 120, and vice versa). In some implementations, one agent (e.g., agent 112) can adopt a Socratic approach, generating prompts (e.g., interaction package 118) that encourage critical thinking and exploration rather than giving direct answers. Another agent (e.g., agent 114) can take an evaluative approach, providing explicit feedback (e.g., interaction package 120) such as confirming correctness or offering the correct solution. Other examples of agent types can include agents configured for motivational support, adaptive pacing, or multimodal responses (e.g., text, audio, or visual cues). By using multiple agents with distinct strategies, server-side compute device 100 can produce diverse and/or complementary interaction packages that enhance personalization and learning outcomes.

In some implementations, agent 112 is a Socratic-style agent configured to generate interaction package 118, and agent 114 is an evaluative-style agent configured to generate interaction package 120. Similarly stated, in some implementations, (1) interaction package 118 (*a*) includes at least one question derived from response 108, biometric data 110, and/or conversation history 116, and (*b*) does not include an evaluation of correction of response 108 while (2) interaction package 120 (*a*) does not include a question and (*b*) includes an assessment of correctness of response 108. In some implementations, where agent 112 is a Socratic-style agent and agent 114 is an evaluative-style agent, interaction package 120 is generated faster and/or with less processing burden than interaction package 118; similarly stated, agent 114 generates interaction package 120 with a lower computational latency than agent 112 generates interaction package 118.

Memory 104 of server-side compute device 100 can also include large language model (LLM) 122. LLM 122 can be implemented (e.g., executed by the processor 102) as a large language model configured to process one or multiple interaction packages (e.g., interaction package 118 and/or 120) generated by agents such as agent 112 and/or 114. LLM 122 (e.g., executed by the processor 102) receives these one or more interaction packages (e.g., interaction package 118 and/or 120) as input and determines how to produce an output responsive to response 108. In some implementations, LLM 122 can select one interaction package directly (e.g., either interaction package 118 or 120), while in other implementations, LLM 122 can combine elements from multiple interaction packages (e.g., both interaction package 118 and 120). The decision-making process for LLM 122 selecting or merging interaction packages can be based on various factors, such as a setting in user U's profile (e.g., preference for Socratic or evaluative style, age, location/geography, school district, and/or the like), instructions from a supervisor (e.g., teacher) of user U, adaptive logic that changes over time (e.g., starting with a Socratic approach early in a session and shifting to evaluative feedback later, or vice versa), biometric data 110, conversation history 116, and/or the like. In some implementations, server-side compute device 100 can include (and/or have access to) a data-storage component—such as a remote or distributed memory store (e.g., a Redis-based store)—that stores data such as conversation history 116, biometric data 110, and/or other state information used during interactions.

Memory 104 of server-side compute device 100 can also include output 124. Output 124 is generated by LLM 122 (e.g., executed by the processor 102) in response to inputting interaction package 118 and/or 120 into LLM 122. Said similarly, output 124 represents the response generated by LLM 122 for response 108. Output 124 can be responsive to response 108 and can take different forms depending on the context. For example, output 124 can indicate whether the user U's answer (response 108) is correct or incorrect, provide a comment or explanation, pose a follow-up question, or offer guidance for improvement. In some cases, output 124 can include multimodal elements such as text, audio, or visual cues.

Output 124 can be sent from server-side compute device 100 to user compute device 140 (e.g., from the processor 102) via network 160. In response to receiving an electronic signal representing output 124 (e.g., at processor 142), user compute device 140 (e.g., using processor 142) can output output 124 (e.g., visually using a display, audibly using a speaker, etc.).

To provide an example with reference to FIG. 1, server-side compute device 100 can send variant 106, such as a math or science problem, to user compute device 140 via network 160. User U interacts with (e.g., reads) variant 106 and provides response 108 using an input mechanism such as a keyboard, touchscreen, or microphone. Before, while, or after the response is provided, sensor 146 on user compute device 140 captures biometric data 110, which can include indicators of attention, stress, or engagement. Server-side compute device 100 stores conversation history 116 and analyzes response 108, biometric data 110, and/or conversation history 116 using two stateless agents—agent 112 and agent 114—each implemented as a different machine learning model. Agent 112 can generate interaction package 118 that encourages further reasoning in a Socratic style, while agent 114 can produce interaction package 120 confirming correctness or suggesting corrections. one or more of these interaction packages 118 and 120 are then processed by LLM 122, which selects or combines interaction packages 118 and 120 based on factors such as user profile settings, teacher preferences, or adaptive logic. The resulting output 124 can indicate whether response 108 is correct, pose a follow-up question, provide guidance, and/or the like before sending output 124 to user compute device 140, delivering a personalized and context-aware learning experience for user U. Alternatively, rather than LLM 122 selecting between multiple interaction packages after the multiple interaction packages have been generated, LLM 122 can determine which agent will generate an interaction package that will be input into output 124 and which agent will not generate an interaction package; similarly stated, the interaction package that will be input into LLM 122 to generate output 124 is generated and another interaction package is not generated.

To provide another example with reference to FIG. 1, server-side compute device 100 sends variant 106, such as the writing prompt: "Write a thesis statement for an essay about renewable energy." User U, on user compute device 140, submits response 108: "Renewable energy is good." Sensor 146 captures biometric data 110, showing signs of low engagement and slight distraction. Conversation history 116 includes prior exchanges where user UJ struggled with vague statements and previously asked, "What makes a thesis strong?" Server-side compute device 100 analyzes response 108, biometric data 110, and/or conversation history 116 using agent 112 and agent 114. Agent 112 (e.g., Socratic) generates interaction package 118 asking, "Can you explain why renewable energy is good and include two reasons in your thesis?" Agent 114 (e.g., evaluative) generates interaction package 120 stating, "Your thesis is too general. A stronger thesis would be: 'Renewable energy reduces carbon emissions and creates sustainable jobs.'" LLM 122 reviews both interaction packages 118 and 120 and selects the Socratic one—interaction package 118. The decision is based on the user's U profile setting (which indicates user U is of an age and/or at a location that prioritizes exploratory learning early in sessions), conversation history 116 (which shows that user U previously asked conceptual questions), and biometric data 110 (which shows signs of low engagement and slight distraction). Output 124 is sent back to user compute device 140 as: "Try adding two reasons why renewable energy is good—what would they be?" This approach encourages deeper thinking while addressing user's U prior struggles with specificity.

To provide another example with reference to FIG. 1, server-side compute device 100 sends variant 106, such as "What is the derivative of $x^2$?" to user compute device 140. User U submits response 108: "$2x^2$." Sensor 146 captures biometric data 110, showing signs of frustration—such as increased heart rate and rapid eye movements—indicating cognitive overload. Conversation history 116 shows user U previously struggled with similar problems and asked for direct help. Agent 112 (e.g., Socratic) generates an interaction package asking, "What rule do you apply when differentiating $x^2$?" Agent 114 (e.g., evaluative) generates an interaction package stating, "Your answer is incorrect; the correct derivative is 2x." LLM 122 selects the evaluative package because (1) biometric data 110 suggests user U is stressed and needs clarity rather than additional questioning and (2) conversation history 116 shows user U asked for direct help. Output 124 is sent back to user compute device 140 as: "Your answer is incorrect; the correct derivative is 2x."

In another scenario, server-side compute device 100 sends variant 106, such as "Write a topic sentence about climate change" to user compute device 140. User U submits response 108: "Climate change is bad." Sensor 146 shows normal engagement, but conversation history 116 reveals user U previously improved when given examples and guided questions. Agent 112 generates a Socratic interaction package: "Can you explain why climate change is bad and include one effect?" Agent 114 generates an evaluative package: "Your sentence is too general. A stronger sentence would be: 'Climate change is accelerating global warming and causing severe weather events.'" LLM 122 merges both interaction packages because conversation history 116 indicates user U benefits from combined guidance and examples. Output 124 becomes: "Your sentence is too general. Try adding one effect, such as global warming or severe weather events—what would you choose and why?"

In some implementations, server-side compute device 100 employs containerized environments to organize and isolate different categories of data and processing tasks. A first set of containers can store variants (e.g., variant 106) and conversation history (e.g., conversation history 116), ensuring that variants and conversation history remain immutable and contextually linked for subsequent analysis. A second set of containers can store stateless agents (e.g., agent 112 and agent 114) and their generated interaction packages (e.g., interaction packages 118 and 120), which are subsequently processed by LLM 122. Containers can be implemented using lightweight virtualization technologies (e.g., Docker or Kubernetes pods) deployed within a virtual private cloud (e.g., containers are hosted locally at server-side compute device 100 and/or stored at a compute device (1) not shown in FIG. 1 and (2) orchestrated by server-side compute device 100) to provide security and isolation. Each container from each set of containers can encapsulate its own dependencies, metadata, and execution environment, allowing horizontal scaling and the support of multiple concurrent sessions. Communication between sets of containers can occur through application programming interfaces (APIs) or message queues, enabling server-side compute device 100 to orchestrate workflows such as sending variants (e.g., variant 106) to user compute device 140, receiving responses (e.g., response 108) and biometric data (e.g., biometric data 110), and routing interaction packages (e.g., interaction packages 118 and 120) to a large language model (e.g., LLM 122) for output (e.g., output 124) generation. This containerized design ensures modularity, fault isolation, and efficient resource utilization while supporting real-time personalization. In some implementations, conversation history 116 is stored at the first set of containers as raw text and/or embeddings.

In some implementations, conversation history 116 can be dynamically managed over time to maintain relevance and improve resource usage. For example, older portions of conversation history 116 can be progressively summarized such that interactions occurring farther in the past are represented in increasingly condensed form. In some implementations, after a predetermined trigger (e.g., a user logging out of their profile, a user shutting down their compute device, passage of a predetermined minimum amount of time, etc.), certain conversations can be deleted entirely. This summarization and deletion process updates the context window ensures that more recent conversations are given more weight. This also preserves instructional context while reducing memory footprint and computational overhead. Thus, conversation history 116 can be updated so that one version of conversation history can be used at one time, and at a later time a different version of conversation history—such as a version that summarizes or deletes older conversation data—is used. By keeping conversation history 116 concise and relevant, server-side compute device 100 and/or user compute device 140 can improve efficiency and support personalization features such as anticipating user text or predicting likely responses based on prior patterns. Summarization can be performed using machine learning models configured to retain certain pedagogical details and engagement indicators while omitting redundant or low-value content, thereby enabling long-term personalization without excessive storage requirements. For example, conversation history 116 can keep track of (e.g., store) the recent (e.g., within a session, within an hour, within a day, within a week, etc.) variants that were sent to user compute device 140 and provided to user U to avoid re-sending the same variant or a substantially similar variant; over time (e.g., as more variants as sent to user compute device 140, as more time passes since that variant was sent to user compute device 140, etc.), however, those variants can be generalized and/or summarized in conversation history 116 (e.g., rather than conversation history 116 storing the exact variant (such as a specific algebra problems with all the variables and coefficients), conversation history 116 can be updated to store more generally what the exact variant was (such as indication that the variant was an algebra problem with two variables)).

In some implementations, for each response, server-side compute device 100 uses two agents—agent 112 and 114—to generate interaction packages. In some implementations, server-side compute device does not use another, third agent to generate an additional interaction package. By using less agents, less interaction packages are generated for LLM 122 to analyze, allowing output 124 to be generated faster. In contrast, in some implementations, additional agents in addition to agents 112 and 114 are used to generate additional interaction packages in addition to interaction packages 118 and 120. For example, a third agent (not illustrated in FIG. 1) can be used to generate a third interaction package (not illustrated in FIG. 1) configured to be input to LLM 122, a fourth agent (not illustrated in FIG. 1) can be used to generate a fourth interaction package (not illustrated in FIG. 1) configured to be input to LLM 122, and/or the like. By using more agents, more interaction packages can be generated that allow LLM 122 to generate a more personalized and/or accurate output 124 for user U.

In some implementations, sensor 146 includes a camera configured to capture video of user U (e.g., before, while, and/or after user U receives variant 106 and/or generates response 108). The video can be encrypted by user compute device 140, and the encrypted video can be sent to server-side compute device 100. In response, server-side compute device 100 can decrypt the encrypted video to obtain an unencrypted version of the video and receive and/or determine biometric data 110 based on the unencrypted version of the video.

In some implementations, sensor 146 includes a camera configured to capture video of user U (e.g., before, while, and/or after user U receives variant 106 and/or generates response 108). The video can be encrypted by user compute device 140 prior to transmission using symmetric encryption (e.g., AES-256). A session-specific symmetric key can be generated on user compute device 140 and then encrypted with server-side compute device 100's public key (e.g., RSA-2048 or ECC-based key) to ensure secure key exchange. The encrypted video and the encrypted session key can be sent to server-side compute device 100. Upon receipt, server-side compute device 100 can use its private key to decrypt the session key and then apply the session key to decrypt the video, obtaining an unencrypted version of the video. Biometric data 110 can then be extracted or determined based on the unencrypted video. In some implementations, integrity checks (e.g., hash-based message authentication code (HMAC) or SHA-256 signatures) can be applied to verify that the video has not been tampered with during transmission. This layered encryption scheme ensures confidentiality, integrity, and secure key management while supporting real-time processing of biometric data.

In some implementations, agent 112 is a machine learning model trained using a first set of one or more prompts and agent 114 is trained using a second set of one or more prompts that is different from the first set of one or more prompts (e.g., where each prompt from the first and second set of prompts can represent and/or be included in an interaction package(s)). For example, agent 112 can be a neural network trained using responses as input training data and interaction packages responsive to the responses in a Socratic-style manner as target learning data. As another example, agent 114 can be a neural network trained using responses as input training data and interaction packages responsive to the responses in an evaluative-style manner as target learning data.

In some implementations, server-side compute device 100 is configured to enforce content safety and privacy standards by filtering out hate speech, biased language, personal identifiers, and/or the like from generated outputs. For example, memory 104 can store a moderation model (e.g., a rule-based model and/or a lightweight classifier) configured to evaluate output 124 against one or more predetermined standards, such as prohibiting profanity, discriminatory or biased language, personally identifiable information. If output 124 fails to satisfy these standards, server-side compute device 100 can automatically update output 124 by removing or replacing the offending portion while preserving the instructional intent. In some cases, the updated output is shorter and reformatted to maintain clarity and compliance.

In some implementations, server-side compute device 100 is configured to evaluate output 124 against an education standard, such as a state education standard in the United States or an equivalent curriculum standard outside the United States. Evaluating against such a standard can include analyzing generated outputs (e.g., output 124) to confirm alignment with grade-level expectations, subject-specific learning objectives, and/or instructional goals defined by the standard. For example, server-side compute device 100 can verify that a math explanation output adheres to the procedural steps and terminology outlined by the relevant standard, or that a reading comprehension prompt includes skills such as citing textual evidence when mandated by the curriculum. This evaluation can be performed using rule-based models or machine learning classifiers trained on annotated examples of standard-aligned content, ensuring that generated outputs satisfy relevant education standards.

In some implementations, at least a portion of generating interaction package 118 and 120 occurs in parallel. Similarly stated, for a non-zero period of time, agent 112 is generating interaction package 118 while agent 114 is generating interaction package 120.

In some implementations, memory 104 of server-side compute device 100 stores an agent router model (not shown in FIG. 1). The agent router model can be a machine learning model configured to determine which agent(s) is used (and not used) to generate an interaction package used to generate output 124. In some implementations, the agent router is configured to analyze conversation history 116, response 108, and/or biometric data 110 to identify whether agent 112 and/or agent 114 will generate an interaction package used to generate output 124. In some implementations, the agent router can be implemented as a machine learning model (e.g., a neural network or decision tree) trained to predict an effective instructional strategy based on real-time context. In some implementations, the agent router can compute engagement indicators from user U's gaze patterns (e.g., indicated in biometric data 110), user U's stress levels from heart rate variability (e.g., indicated in biometric data 110), and/or linguistic indicators from user U's response (e.g., indicated in response 108 and/or conversation history 116). These indicators can be analyzed by the agent router to determine whether the user U would benefit more from, for example, exploratory guidance, direct corrective feedback, or whatever other style agent 112 or 114 has been configured to deploy. If, for example, the analysis indicates high engagement and curiosity, the agent router can select agent 112 (e.g., Socratic-style) to generate prompts that encourage reasoning. If, for another example, the analysis suggests frustration or cognitive overload, however, the agent router can select agent 114 (e.g., evaluative-style) to provide clear, corrective feedback.

In some implementations, the agent router can select one stateless agent (e.g., agent 112) over another agent (e.g., agent 114) based on demographic attributes such as the age or geographic location of user U. For example, memory 104 or 144 can store a user profile that includes an indication of user U's age and location (e.g., region, state, city, school district, etc.). The agent router can analyze this profile (e.g., in combination with conversation history 116, response 108, and biometric data 110) to determine which instructional style to employ for user U. For instance, if user U is a younger learner, the agent router can select an agent configured for simplified, step-by-step guidance, whereas for an older learner, the agent router can select an agent configured for more advanced or exploratory prompts. Similarly, geographic information can influence language style, cultural context, or curriculum alignment; for example, the agent router can select an agent trained to provide examples relevant to user U's region or to comply with local educational standards.

In some implementations, if a first agent was used to generate an output that resulted in an unsatisfactory response, a second, different agent can be used to respond. For example, if agent 112 (and not agent 114) was used to generate output 124, and user U's response to output 124 fails to satisfy a criterion (e.g., the response is correct, the response included a predetermined keyword, the response exceeds a predetermined minimum number of words, etc.), user U's response to output 124 can be analyzed using agent 114 (and not agent 112) to generate an interaction package and output responsive to user U's response to output 124.

In some implementations, server-side compute device 100 can be tested using simulated evaluations to validate instructional quality and interaction flow. For example, testing can include verifying data flow between server-side compute device 100 and user compute device 140 to ensure that exchanges involving variant 106, response 108, and output 124 occur in an intended sequence (e.g., variant 106 is generated first, response 108 is generated second, and output 124 is generated third). In some cases, LIMs can be configured to "act" as simulated student personas (e.g., a highly engaged student who provides detailed answers and asks follow-up questions; a struggling student who frequently submits vague or incorrect responses; a student with low confidence who often asks for hints before attempting an answer; a student who expresses frustration or confusion about the clarity of variant 106) and interact with stateless agents such as agent 112 and agent 114 to emulate realistic learning scenarios. For example, a simulated persona representing a rushed student can respond to variant 106 with a one-word answer like "yes" or "done," prompting agent 112 to generate interaction package 118 that encourages elaboration (e.g., "Can you explain your reasoning?"). As another example, a simulated student persona representing a student who often expresses frustration or confusion can generate a response indicating that variant 106 is confusing or hard to understand, prompting agent 112 to adjust interaction package 118 to include clarifying questions and/or agent 114 to modify interaction package 120 to provide additional explanatory feedback. In some implementations, an LLM configured to "act" as a judge can review outputs (e.g., output 124) generated by LLM 122 against a predefined set of criteria, such as clarity, correctness, engagement level, and alignment with pedagogical objectives. These evaluations help identify desirable qualities in responses-such as encouraging reasoning, providing accurate feedback, and maintaining tone consistency—and assess whether outputs are appropriate for a given user's context. For example, the LLM judge can evaluate output 124 based on whether output 124 provides constructive feedback, aligns with grade-level standards, and maintains an encouraging tone. This testing framework enables iterative refinement of agent logic, interaction packages, and personalization strategies.

Although FIG. 1 illustrates two compute devices, in other implementations, more or less compute devices can be used. For example, in some implementations, a single compute device can perform the functions of server-side compute device 100 and user compute device 140. As another example, in some implementations, the functions of server-side compute device 100 and/or user compute device 140 can be divided across multiple compute devices.

Figure 2A:
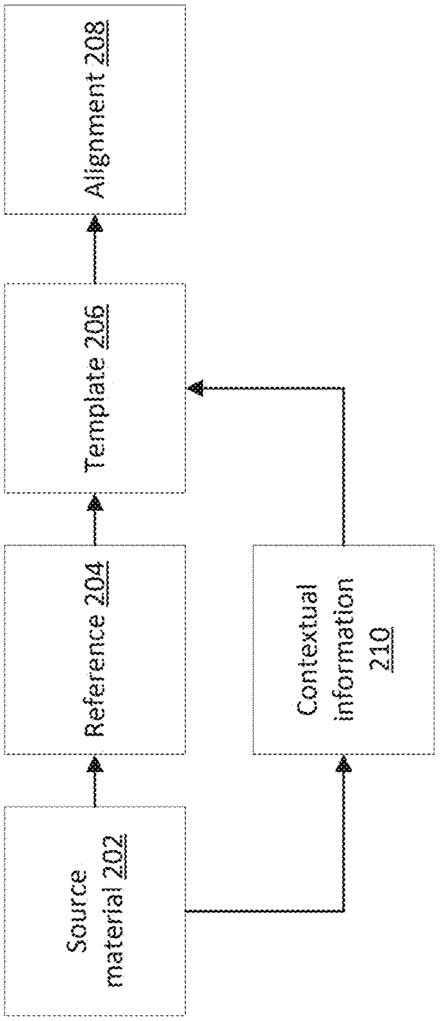
FIG. 2A illustrates a flow chart for generating a template for a variant, according to an embodiment.

FIG. 2A illustrates a flow chart for generating a template for a variant, according to an embodiment. FIG. 2A illustrates source material 202, reference 204, template 206, alignment 208, and contextual information 210, each of which can be stored in memory (e.g., memory 104, memory 144, and/or a memory of a compute device not illustrated in FIG. 1) accessible by a processor (e.g., processor 102, processor 142, and/or a processor of a compute device not illustrated in FIG. 1) such that the processor can execute the various components. Variant 216 can be similar in structure and/or function as variant 106 of FIG. 1. In some implementations, variant 216 is generated by server-side compute device 100 of FIG. 1. As such, the processes and/or steps shown and described with respect to FIGS. 2A and 2B can be represented as code stored in memory 104 and executed by processor 102 of FIG. 1).

Source material 202 can represent the content (e.g., educational content) that can be used to generate variant 216. Source material 202 can be, for example, a textbook, learning guide, or instructional materials containing text, mathematical notations, scientific notations, images, audio, video, diagrams, and structured exercises, and/or the like. A compute device (e.g., server-side compute device 100, user compute device 140, and/or a compute device not shown in FIG. 1) partitions source material 202 into smaller, context-preserving segments. For example, a math textbook chapter on fractions can be divided into individual problems, explanatory text, and associated images, each tagged with metadata such as chapter, section, and sub-section identifiers. This partitioning ensures that subsequent steps maintain pedagogical integrity while enabling fine-grained control over content generation. In some implementations, source material 202 includes a table of contents, where source material 202 is partitioned based on (e.g., according to) the table of contents (e.g., partitioning each chapter, partitioning each section of each chapter, partitioning each subsection of each section, and/or the like).

Reference 204 is extracted content from source material 202 that represents a specific instructional item, such as an example problem or concept. Reference 204 serves as the starting point for creating template 206. Said similarly, reference 204 serves as an example problem that variant 216 can be generated based on. For instance, if source material 202 is a textbook on algebra, reference 204 could be "Solve for x: 3x+5=20."

Contextual information 210 represents context of source material 202. Contextual information 210 enriches template 206 with details about the instructional environment in which reference 204 appears. Contextual information 210 can include chapter titles, section titles within chapters, sub-section titles within sections, and/or the like provided in source material 202. For example, if reference 204 appears in a section of source material 202 introducing linear equations, contextual information 210 is used to ensure that template 206 is also related to (e.g., in the context of) linear equations. This link prevents decontextualization.

Template 206 represents a structured blueprint derived from reference 204. Template 206 can be for different subjects (e.g., algebra, geometry, science, language arts, history, music, etc.), modalities (e.g., text, images, audio, video, interactive games, etc.), and/or levels (e.g., various grades for various states). Template 206 specifies the components of reference 204, such as question text, solution steps, question stem, answer choices, distractors (or foils), variables, values, images, and/or the like. For example, a template for reference 204 "Solve for x: 3x+5=20" can define placeholders for coefficients (e.g., 3, 5, and 20) and constants (e.g., x), enabling systematic variation (e.g., varying coefficients) while preserving problem structure (e.g., not varying constants). As another example, if reference 204 asks "What is the main theme of the passage?" with four answer choices, template 206 can capture the question stem, the correct answer choice, and the logic behind the three incorrect answer choices.

In some implementations, a machine learning model is configured to automatically extract the structured blueprint from reference 204 and identify which components of reference 204 can be varied and not varied. The machine learning model can include a sequence of steps such as: (i) parsing the reference 204 into semantic units (e.g., question stem, solution steps, answer choices, distractors, variables, and images); (ii) applying natural language processing (NLP) to classify each unit as fixed or variable based on linguistic patterns and/or metadata; and (iii) generating placeholders for variable elements while locking fixed elements to maintain pedagogical consistency. For example, the machine learning model can use dependency parsing and/or named entity recognition to detect numeric values (e.g., coefficients) and symbolic constants (e.g., "x") in a math problem, then tag coefficients as variable and constants as fixed. Similarly, for a reading comprehension question, the machine learning model can identify the question stem and correct answer as fixed while marking distractors as variable, using attention-based scoring to determine which distractors can be replaced without altering the instructional goal. The machine learning model can be trained using supervised learning with annotated examples of references (e.g., questions) and templates, where the training data includes labels for variable versus fixed components.

In some implementations, contextual information 210 includes a summary of a chapter in source material 202 where reference 204 was found, section within the chapter where reference 204 was found, sub-section within the section where reference 204 was found, and/or the like. In some implementations, the summary can be generated using a machine learning model (e.g., LLM) configured to receive input (e.g., the chapter, the section, the sub-section, etc.) and output summaries (e.g., of the chapter, of the section, of the sub-section, etc.). In some implementations, template 206 is generated based on contextual information 210 such that, for example, template 206 is at a level or complexity predetermined to be appropriate for a user (e.g., student). In some implementations, if contextual information 210 includes a summary of a chapter in source material 202, section within the chapter, sub-section within the section, and/or the like, template 206 can be generated based on the summary (and not all of source material 202, which can reduce processing burden and increase processing efficiency). For example, if the summary of a chapter indicates that the chapter's goal is to solve algebra problems with two variables, template 206 can be generated to include two variables.

Alignment 208 can be metadata that links and/or associates template 206 to one or more educational standards. For example, alignment 208 can be metadata indicating that template 206 satisfies a first standard and is related to a second standard. Determining alignment 208 can include an LLM alignment, where an LLM (e.g., different than LLM 122; stored at memory 104, 144, or a memory not shown in FIG. 1 and executed by a processor such as processor 102) trained with reinforcement learning predicts hierarchical relationships between templates (e.g., template 206) and educational standards.

Determining alignment 208 can additionally or alternatively include a graph database expansion, where a graph database (e.g., stored at memory 104, 144, or a memory not shown in FIG. 1) stores relationships between standards and concepts (or templates). In some implementations, after LLM determines alignment 208, the graph database expands coverage (e.g., updates alignment 208) by linking templates to related standards not explicitly covered in the training set of the LLM.

Figure 2B:
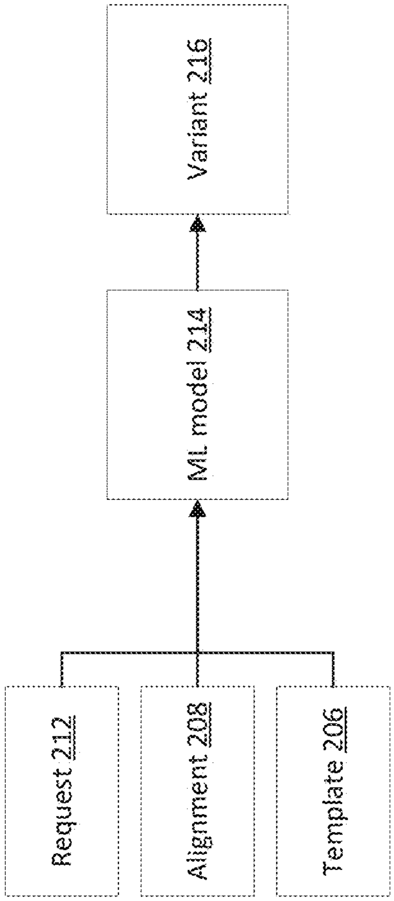
FIG. 2B illustrates a flow chart for generating a variant, according to an embodiment.

FIG. 2B illustrates a flow chart for generating a variant, according to an embodiment. FIG. 2B includes template 206, alignment 208, request 212, ML model 214, and variant 216, each of which can be stored in memory (e.g., memory 104, memory 144, and/or a memory of a compute device not illustrated in FIG. 1) accessible by a processor (e.g., processor 102, processor 142, and/or a processor of a compute device not illustrated in FIG. 1), such that the processor can execute the various components. Request 212 represents a trigger for generating a variant (e.g., variant 216). Request 212 can originate from a user (e.g., user U, user U's teacher, etc.) or compute device (e.g., user compute device 140, server-side compute device 100, etc.) seeking additional practice problems. Request 212 can include parameters such as problem type, complexity, or preferred format (e.g., text-only or text with images). For example, a user (e.g., student or teacher) can request (e.g., using user compute device 140 or a compute device not shown in FIG. 1) as request 212: "a problem on linear equations suitable for grade 8." Request 212 can also indicate a geography (e.g., state, country, district, etc.) so that the variant is generated in alignment with the standards of that geography (e.g., comply with that state's education standards).

In some implementations, alignment 208 and template 206 are chosen based on request 212. For example, a compute device (e.g., server-side compute device 100, user compute device 140, and/or a compute device not shown in FIG. 1) can include a library of various templates and associated alignments. When a request is received (e.g., request 212), the compute device can determine which template and alignment can be used to process that request. In some implementations, this determination can also consider geography information included in request 212 so that the selected template 206 and alignment 208 comply with the educational standards applicable to that region (e.g., a U.S. state's standards). In some implementations, a neural network can be configured to receive requests and identify the template and alignment to be used with that request, where the neural network is trained using requests as input learning data and associated templates and alignments are target learning data. The neural network can further incorporate metadata representing geography-specific standards determined based on request 212 to ensure that generated variants reflect appropriate terminology, difficulty level, and/or standards for the indicated region.

ML model 214 is configured to generate variants based on request 212, alignment 208, and/or template 206. ML model 214 uses request 212, alignment 208, and/or template 206 to output variant 216, where variant 216 is similar to reference 204 but sufficiently different to provide fresh practice. For example, given a template or reference for "Solve for x: 3x+5=20," ML model 214 can generate "Solve for x: 4x+7=23."

In some implementations, ML model 214 employs a random seeding mechanism to introduce controlled variability, ensuring that multiple distinct variants can be generated from the same template (e.g., template 206). For example, ML model 214 can generate (1) variant 216 based on request 212, alignment 208, template 206, and a first random number, and (2) also generate a different variant based on request 212, alignment 208, template 206, and a second random number different than the first random number.

Variant 216 is a standards-aligned problem that can include text and/or images. Variant 216 can be validated for correctness before delivery (e.g., to user compute device 140). For example, in some implementations, after variant 216 is generated, a process reward model (e.g., accessible by processor 102, processor 142, and/or a processor not shown in FIG. 1) validates correctness of the solution steps for variant 216 produced by ML model 214, checking for logical consistency and accuracy. In some implementations, process reward model can include one or more LLMs used to evaluate quality of intermediate steps in a reasoning process (e.g., the process to answer variant 216). In some implementations, the process reward model acts as a quality gate by reviewing each step of the solution to ensure that the reasoning follows proper rules and that the final answer matches the expected result. If any inconsistency or error is detected, variant 216 can be flagged or regenerated before being sent to the user's compute device. This validation process helps prevent incorrect or unsolvable problems from reaching the user and ensures reliability of generated content.

When source material 202 includes images, the compute device (e.g., server-side compute device 100, user compute device 140, and/or a compute device not shown in FIG. 1) embeds each image into a vector space and clusters similar images (e.g., number lines or geometric shapes). This clustering enables ML model 214 to reproduce images with modified parameters. For example, if the original problem (e.g., response 108) includes an angle of 70°, variant 216 can include an angle of 50° while maintaining visual accuracy and/or resemblance to the original problem. This process ensures that image-based problems remain visually consistent.

In some implementations, generating a variant from an image-based reference includes multiple steps. First, the reference image (e.g., reference 204) is extracted from source material 202 and contextual information 210 (e.g., chapter summary or instructional goal where the reference image appears) is determined. The reference image is then transformed into a template (e.g., template 206) that specifies which visual elements can vary (e.g., angle size, shape dimensions) and not vary. The template is aligned (e.g., using an LLM and a graph database) to generate an aligned template, where the LLM is trained using reinforcement learning to align template text (which can include generated captions of the image in the template). The image from the aligned template is embedded into a vector space, and the embedding is assigned to a cluster from a plurality of clusters (each cluster from the plurality of clusters representing unique image types). Said similarly, the aligned template is converted into a numerical representation that captures its visual features (such as shapes, angles, and proportions). This numerical representation is compared against a set of predefined groups of similar images (clusters), such as number lines, geometric figures, or graphs. ML model 214 then uses the aligned template, cluster indication, and contextual information to generate a variant image with modified parameters (e.g., assigning the aligned template to a cluster helps ML model 214 understand the type of image and apply transformations consistent with images of the same cluster). In some implementations, ML model 214 is configured create images for that cluster (e.g., for images clustered into a group of triangles, ML model 214 creates a "triangle tool model" and ML model 214 provides the inputs to the triangle tool model to create a triangle image with modified parameters). Said similarly, ML model 214 is configured to generate other models configured to generate images for clusters, such as a first model configured to generate images of isosceles triangles for clusters including images of isosceles triangles, a second model configured to generate images of vectors for clusters including images of vectors, and/or the like.

To provide an example, consider a reading comprehension question (reference 204) extracted from a language arts textbook (source material 202): "What is the main theme of the passage?" with four answer choices. A template (template 206) is generated that captures the question stem, the correct answer, and the distractors, along with contextual information (contextual information 210) such as the chapter title ("Themes in Literature") and instructional objectives (e.g., "Identify central themes in narrative text"). The template is then aligned (alignment 208) to educational standards using two technologies. First, an LLM trained with reinforcement learning predicts which standards the template satisfies. For example, the LLM determines that the question aligns to a standard requiring students to identify a theme or central idea of a text and explain how it is conveyed through details. Further, a graph database expands the alignment by linking the template to related standards. For instance, if the template aligns to a theme-identification standard, the graph database can also link the template to standards for citing textual evidence or analyzing character development. This does not change the original reading comprehension question but creates alignment metadata that enables variants to be generated that incorporate these related skills. The ML model (ML model 214) then uses the request, template, and alignment to produce a variant (variant 216) such as: "What is the main theme of the passage?Provide one detail from the text that supports your answer." This variant satisfies both the original theme-identification standard and the related textual-evidence standard identified during alignment. The process reward model then validates the solution steps to ensure correctness before the variant is delivered (e.g., to user compute device 140).

Figure 3:
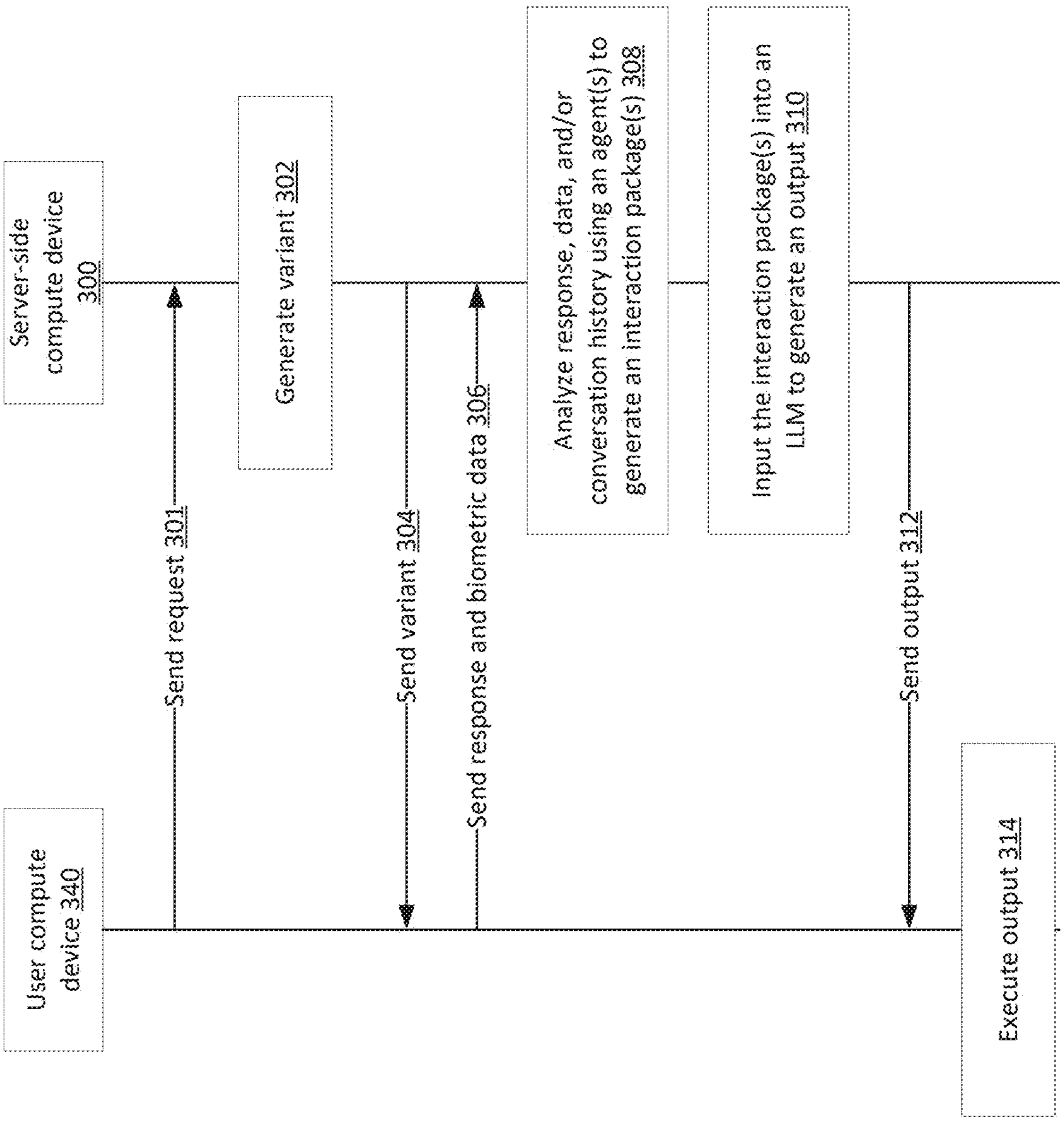
FIG. 3 illustrates data flow between a user compute device and a server-side compute device, according to an embodiment.

FIG. 3 illustrates data flow between a user compute device and a server-side compute device, according to an embodiment. User compute device 340 can be similar in function and/or structure as user compute device 140. Server-side compute device 300 can be similar in function and/or structure as server-side compute device 340. As such, steps shown as being executed at user compute device 340 can be executed by a processor such as processor 142 and steps shown as being executed by server-side compute device 300 can be executed by a processor such as processor 102, shown in FIG. 1).

At 301, user compute device 340 sends a request (e.g., request 212) to server-side compute device 300. At 302, server-side compute device 300 generates a variant (e.g., variant 106 or 216) based on the request. In some implementations, the variant can be generated similar to the process shown and described with respect to FIGS. 2A and 2B. At 304, an electronic signal representing the variant is sent (e.g., via network 160) from server-side compute device 300 to user compute device 340. At 306, user compute device 340 sends (e.g., via network 160) a response (e.g., response 108) and data associated with the user (e.g., biometric data 110) to server-side compute device 300. At 308, server-side compute device 300 analyzes the response, data associated with the user, and/or conversation history (e.g., conversation history 116) using an agent(s) (e.g., agent 112 and/or 114) to generate an interaction package(s) (e.g., interaction package 118 and/or 120). At 310, the interaction package(s) is input into an LLM (e.g., LLM 122) to generate an output (e.g., output 124). At 312, an electronic signal representing the output is sent (e.g., via network 160) from server-side compute device 300 to user compute device 340. At 314, user compute device 340 executes (e.g., outputs to user U) the output.

Figure 4:
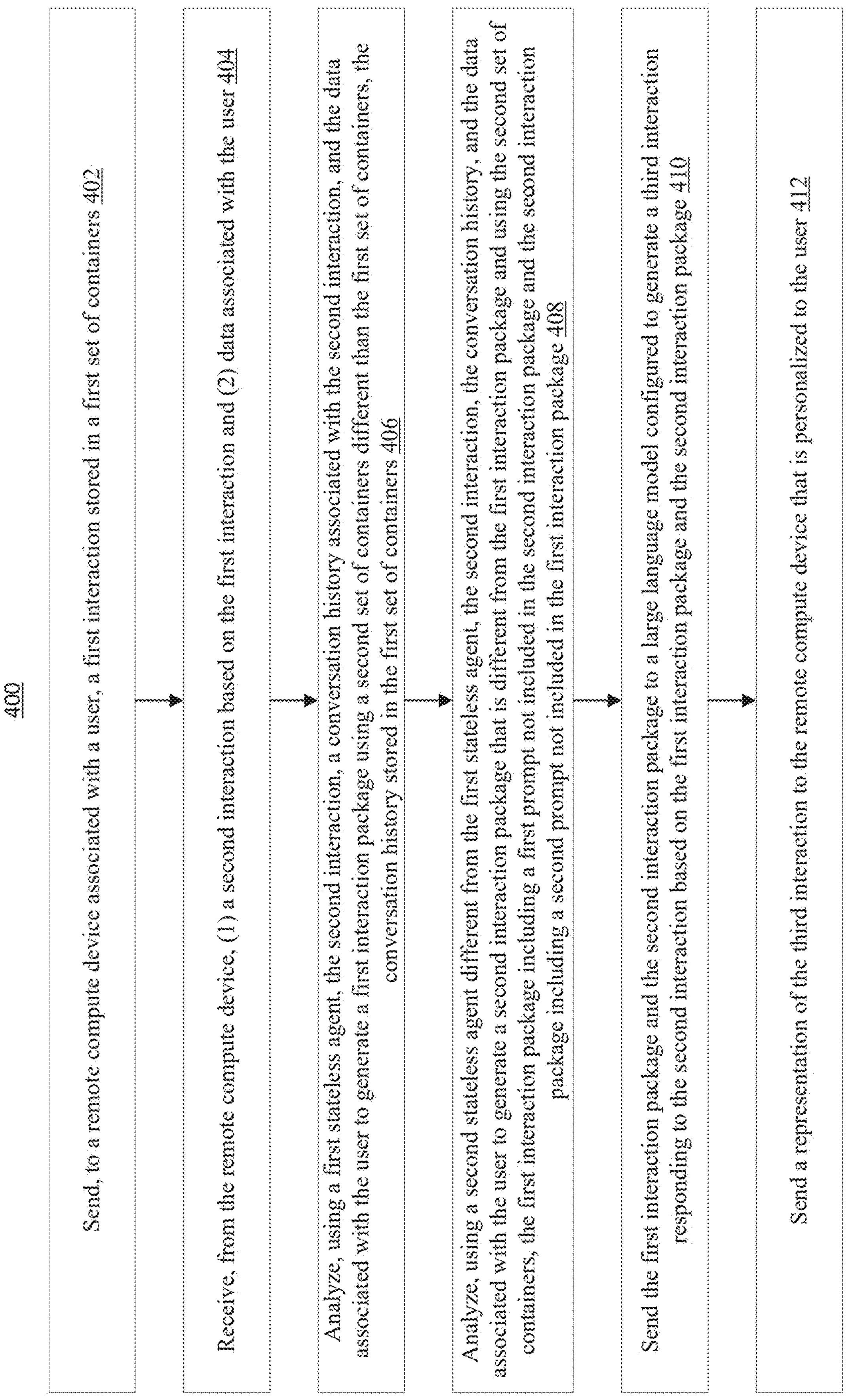
FIG. 4 illustrates a flowchart of a method to generate personalized interactions, according to an embodiment.

FIG. 4 illustrates a flowchart of a method 400 to generate personalized interactions, according to an embodiment. In some implementations, method 400 is stored in memory (e.g., memory 104) and executable by a processor (e.g., processor 102).

At 402, a first interaction (e.g., variant 106 or 216) stored in a first set of containers is sent to a remote compute device (e.g., user compute device 140) associated with a user (e.g., user U). At 404, (1) a second interaction (e.g., response 108) based on the first interaction and (2) data (e.g., biometric data 110) associated with the user are received from the remote compute device. At 406, the second interaction, a conversation history (e.g., conversation history 116) associated with the second interaction, and the data associated with the user are analyzed using a first stateless agent (e.g., agent 112) to generate a first interaction package (e.g., interaction package 118) using a second set of containers different than the first set of containers. The conversation history is stored in the first set of containers. At 408, the second interaction, the conversation history, and the data associated with the user are analyzed using a second stateless agent (e.g., agent 114) different from the first stateless agent to generate a second interaction package (e.g., interaction package 120) that is different from the first interaction package and using the second set of containers. The first interaction package includes a first prompt not included in the second interaction package and the second interaction package includes a second prompt not included in the first interaction package. At 410, the first interaction package and the second interaction package are sent to a large language model (e.g., LLM 122) configured to generate a third interaction (e.g., output 124) responding to the second interaction based on the first interaction package and the second interaction package. At 412, a representation of the third interaction is sent to the remote compute device that is personalized to the user.

Some implementations of method 400 further include refraining from analyzing the second interaction, the conversation history, and the data associated with the user using a third stateless agent different than the first stateless agent and the second stateless agent while the first interaction package and the second interaction package are being generated.

Some implementations of method 400 further include receiving encrypted video from the remote compute device and decrypting the encrypted video to obtain an unencrypted video. The data associated with the user can be represented in the unencrypted video.

In some implementations of method 400, the first stateless agent is trained using a first plurality of prompts and the second stateless agent is trained using a second plurality of prompts different from the first plurality of prompts.

Some implementations of method 400 further include determining, using a rule-based model, that the third interaction fails to satisfy at least one predetermined standard. Some implementations of method 400 further include updating the third interaction to generate the representation of the third interaction. The representation of the third interaction (1) satisfies the at least one predetermined standard and (2) is shorter than the third interaction.

In some implementations of method 400, the first interaction package includes at least one question derived from the second interaction, the data associated with the user, and the conversation history. The first interaction package does not include an evaluation of correctness of the second interaction. The second interaction package includes the evaluation of correctness of the second interaction, and the second interaction package does not include a question.

In some implementations of method 400, the second stateless agent is configured to generate the second interaction package with a lower computational latency than the first stateless agent.

In some implementations of method 400, the first set of containers and the second set of containers are deployed within a virtual private cloud.

Figure 5A:
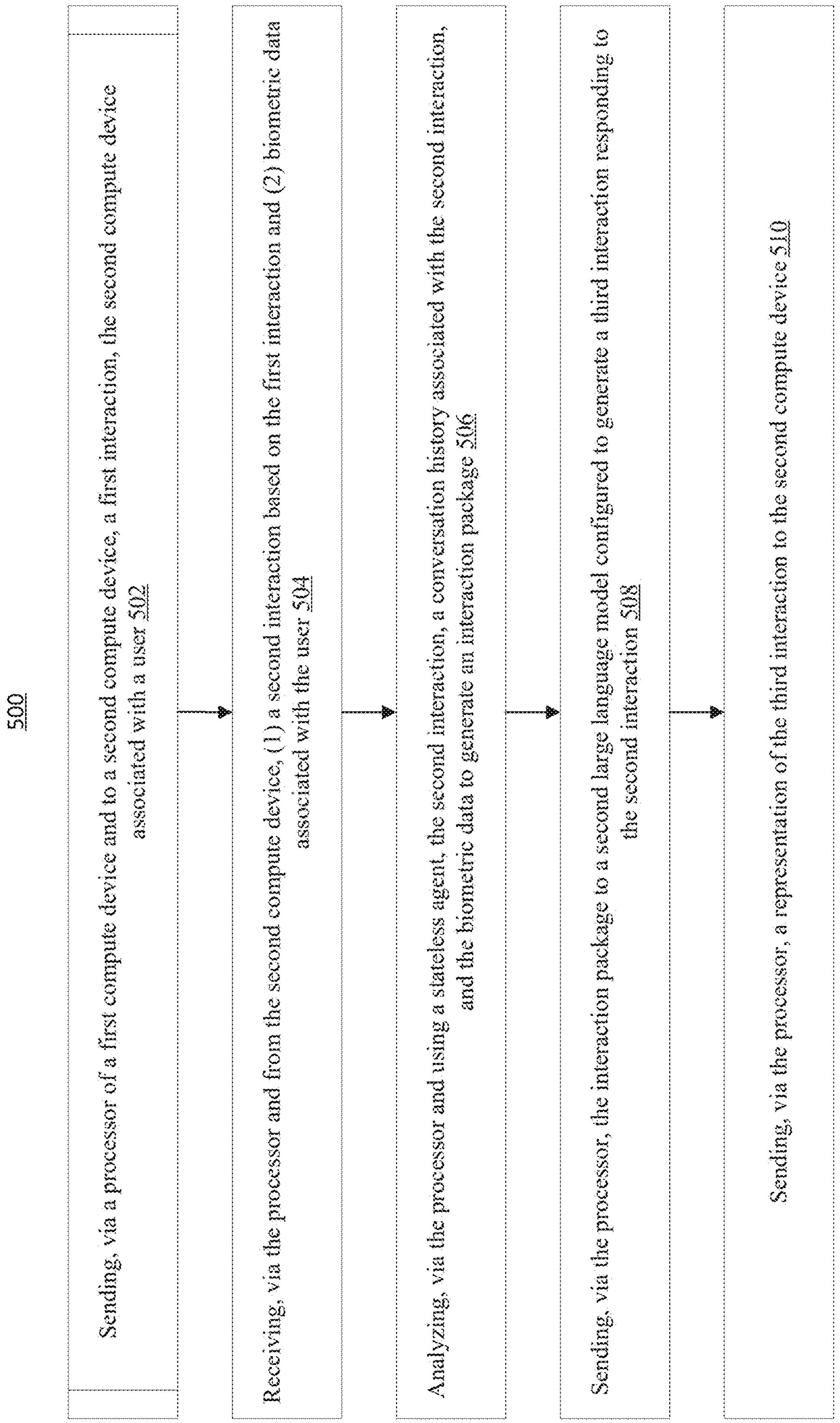
FIGS. 5A and 5B illustrate a flowchart of a method to generate an interaction, according to an embodiment.
Figure 5B:
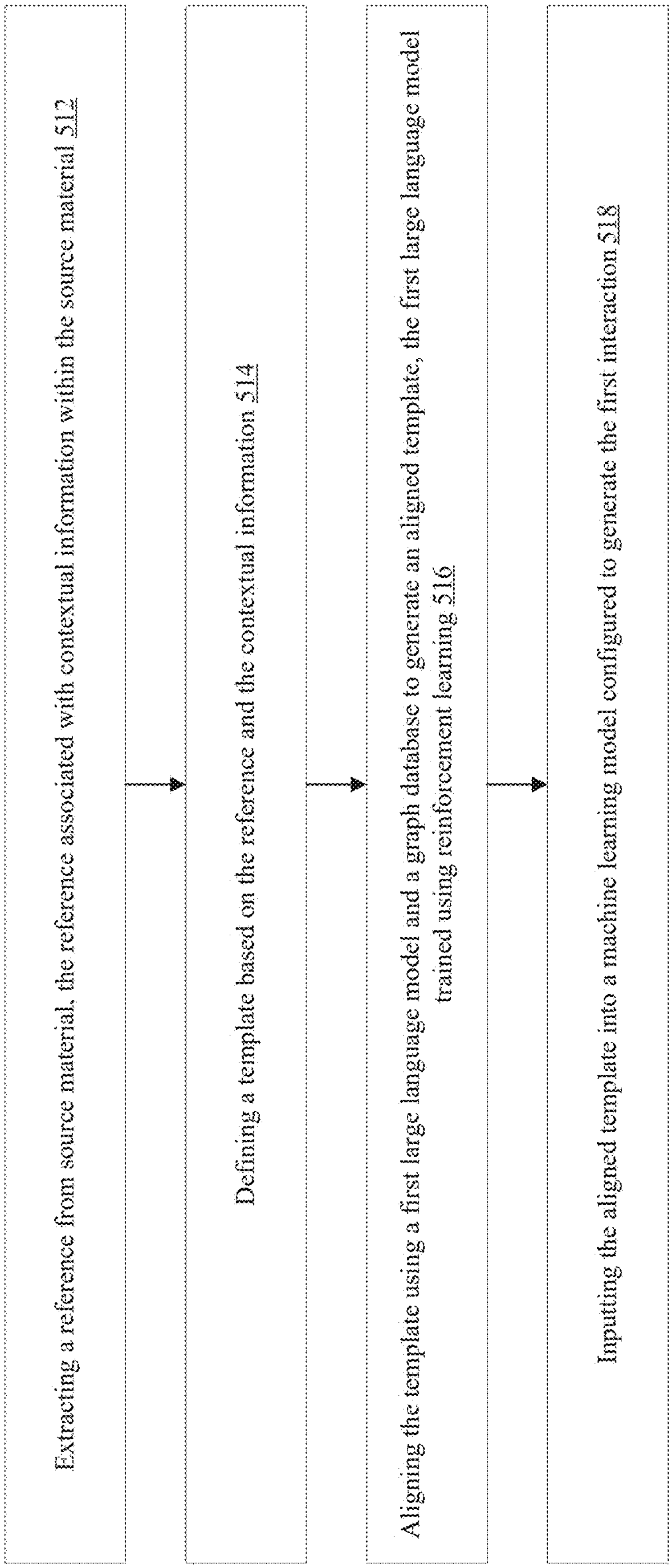

FIGS. 5A and 5B illustrate a flowchart of a method 500 to generate an interaction, according to an embodiment. In some implementations, method 500 is stored in memory (e.g., memory 104) executable by a processor (e.g., processor 102).

At 502, a first interaction (e.g., variant 106 or 216) is sent via a processor (e.g., processor 102) of a first compute device (e.g., server-side compute device 100) to a second compute device (e.g., user compute device 140). The second compute device is associated with a user (e.g., user U).

FIG. 5B illustrates a flowchart to generate the first interaction. At 512, a reference (e.g., reference 204) is extracted from source material (e.g., source material 202). The reference is associated with contextual information (e.g., contextual information 210) within the source material. At 514, a template (e.g., template 206) is defined based on the reference and the contextual information. At 516, the template is aligned using a first large language model and a graph database to generate an aligned template (e.g., alignment 208). The first large language model is trained using reinforcement learning. At 518, the aligned template is input to a machine learning model (e.g., ML model 214) configured to generate the first interaction.

Returning to FIG. 5A, at 504, (1) a second interaction (e.g., response 108) based on the first interaction and (2) biometric data (e.g., biometric data 110) associated with the user are received via the processor and from the second compute device. At 506, the second interaction, a conversation history (e.g., conversation history 116) associated with the second interaction, and the biometric data are analyzed via the processor and using a stateless agent (e.g., agent 112) to generate an interaction package (e.g., interaction package 118). At 508, the interaction package is sent, via the processor, to a second large language model (e.g., LLM 122) configured to generate a third interaction (e.g., output 124) responding to the second interaction. At 510, a representation of the third interaction is sent, via the processor, to the second compute device.

In some implementations of method 500, the interaction package is generated using a first set of containers, and the conversation history and the first interaction are stored at a second set of containers different from the first set of containers.

In some implementations of method 500, the stateless agent is a first stateless agent and the interaction package is a first interaction package. Some implementations of method 500 further include analyzing, via the processor and using a second stateless agent (e.g., agent 114) different from the first stateless agent, the second interaction, the conversation history, and the biometric data to generate a second interaction package (e.g., interaction package 120) that is different from the first interaction package. Some implementations of method 500 further include sending, via the processor, the second interaction package to the second large language model. The second large language model is further configured to generate the third interaction based on the second interaction package.

In some implementations of method 500, the stateless agent is a first stateless agent and the interaction package is a first interaction package. Some implementations of method 500 further include analyzing, via the processor and using a second stateless agent (e.g., agent 114) different from the first stateless agent, the second interaction, the conversation history, and the biometric data to generate a second interaction package (e.g., interaction package 120) that is different from the first interaction package. Some implementations of method 500 further include sending, via the processor, the second interaction package to the second large language model. The second large language model is further configured to generate the third interaction based on the second interaction package.

Some implementations of method 500 further include analyzing, via the processor, at least one of the second interaction or the biometric data to identify the stateless agent from a plurality of stateless agents (e.g., agent 112, 114). The analyzing of the second interaction, the conversation history, and the biometric data to generate the interaction package occurs (1) in response to identifying the stateless agent from the plurality of stateless agents and (2) without using remaining agents from the plurality of stateless agents.

Some implementations of method 500 further include receiving a profile representing the user. The profile indicates at least one of an age of the user or a geography of the user. Some implementations of method 500 further include analyzing, via the processor, the profile and at least one of the second interaction or the biometric data to identify the stateless agent from a plurality of stateless agents. The analyzing of the second interaction, the conversation history, and the biometric data to generate the interaction package occurs (1) in response to identifying the stateless agent from the plurality of stateless agents and (2) without using remaining agents from the plurality of stateless agents.

In some implementations of method 500, generating the first interaction at 502 further includes validating the first interaction using a process reward model. The first interaction is sent to the second compute device in response to validating the first interaction.

In some implementations of method 500, analyzing the second interaction, the conversation history, and the biometric data to generate the interaction package at 506 includes determining a state of the user based on the biometric data. The state indicates a distraction level of the user.

In some implementations of method 500, the stateless agent is a first stateless agent and the interaction package is a first interaction package. Some implementations of method 500 further include receiving, via the processor and from the second compute device, a fourth interaction responding to the representation of the third interaction. Some implementations of method 500 further include determining, via the processor, that the fourth interaction fails to satisfy a criterion. Some implementations of method 500 further include analyzing, via the processor, in response to determining that the fourth interaction fails to satisfy the criterion, and using a second stateless agent (e.g., agent 114) different from the first stateless agent, the conversation history and the fourth interaction to generate a second interaction package (e.g., interaction package 120). Some implementations of method 500 further include sending, via the processor, the second interaction package to the second large language model to generate a fifth interaction responding to the fourth interaction. Some implementations of method 500 further include sending, via the processor, a representation of the fifth interaction to the second compute device.

Figure 6:
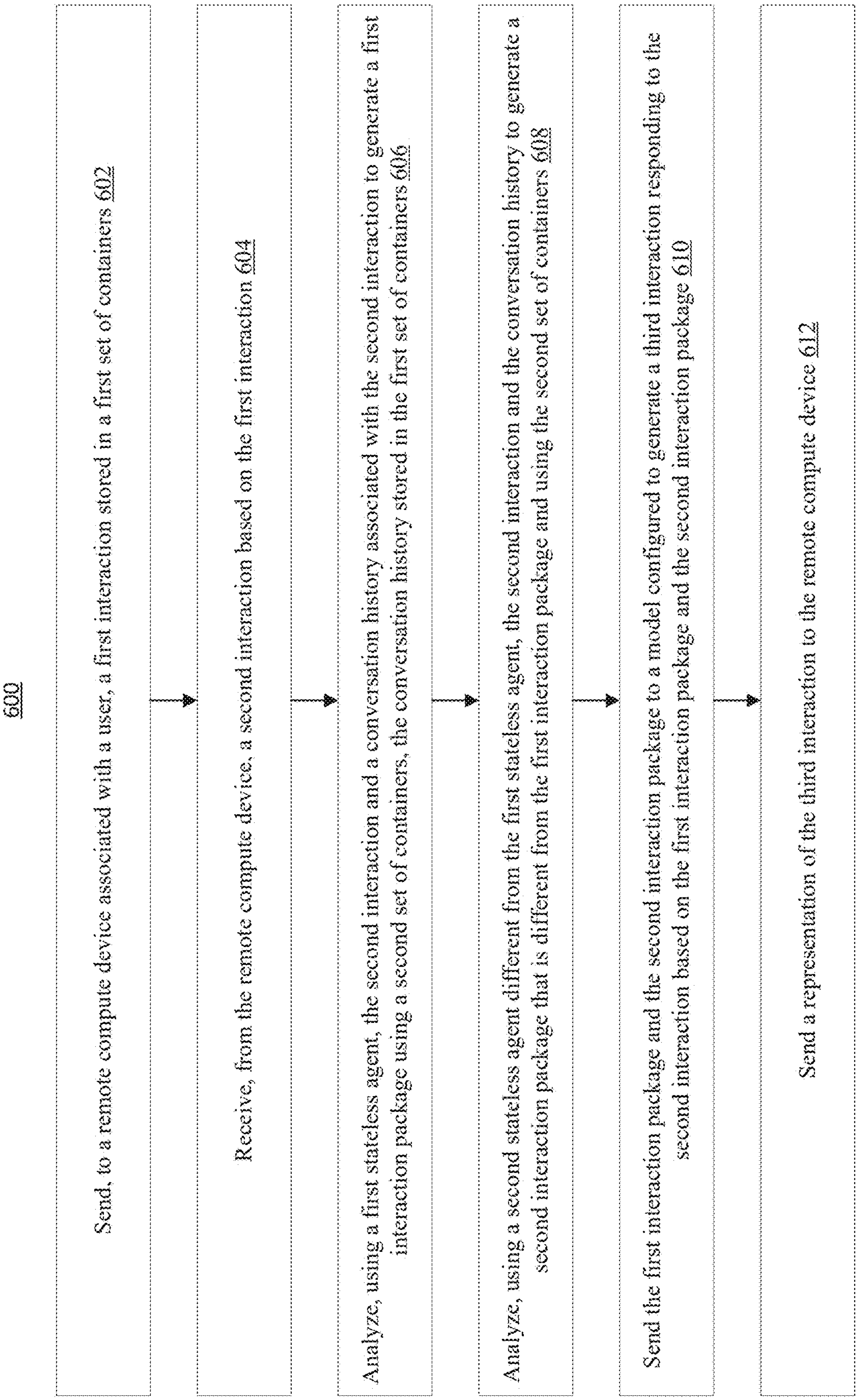
FIG. 6 illustrates a flowchart of a method to generate interaction packages, according to an embodiment.

FIG. 6 illustrates a flowchart of a method 600 to generate interaction packages, according to an embodiment. In some implementations, method 600 is stored in memory (e.g., memory 104) executable by a processor (e.g., processor 102).

At 602, a first interaction (e.g., variant 106 or 216) stored in a first set of containers is sent to a remote compute device (e.g., user compute device 140) associated with a user (e.g., user U). At 604, a second interaction (e.g., response 108) based on the first interaction is received from the remote compute device. At 606, the second interaction and a conversation history (e.g., conversation history 116) associated with the second interaction are analyzed using a first stateless agent (e.g., agent 112) to generate a first interaction package (e.g., interaction package 118) using a second set of containers. The conversation history is stored in the first set of containers. At 608, the second interaction and the conversation history are analyzed using a second stateless agent (e.g., agent 114) different from the first stateless agent to generate a second interaction package (e.g., interaction package 120) that is different from the first interaction package and using the second set of containers. At 610, the first interaction package and the second interaction package are sent to a model (e.g., LLM 122) configured to generate a third interaction (e.g., output 124) responding to the second interaction based on the first interaction package and the second interaction package. At 612, a representation of the third interaction is sent to the remote compute device.

In some implementations of method 600, generating the first interaction includes extracting a reference (e.g., reference 204) from source material (e.g., source material 202). The reference is associated with contextual information (e.g., contextual information 210) within the source material. The reference is an image. Generating the first interaction further includes transforming the reference into a template (e.g., template 206). Generating the first interaction further includes aligning the template using a large language model and a graph database to generate an aligned template. The large language model is trained using reinforcement learning. Generating the first interaction further includes embedding the aligned template to generate an embedding. Generating the first interaction further includes assigning the embedding to a cluster from a plurality of clusters. Generating the first interaction further includes inputting the aligned template, an indication of the cluster, and the contextual information into a machine learning model (e.g., ML model 214) to generate the first interaction.

In some implementations of method 600, the first interaction package includes a prompt to assist the user with the first interaction without providing an answer to the first interaction, and the second interaction package includes a prompt to provide the answer to the first interaction if the second interaction differs from the answer.

Combinations of the foregoing concepts and additional concepts discussed here (provided such concepts are not mutually inconsistent) are contemplated as being part of the subject matter disclosed herein. The terminology explicitly employed herein that also may appear in any disclosure incorporated by reference should be accorded a meaning most consistent with the particular concepts disclosed herein.

The drawings primarily are for illustrative purposes, and are not intended to limit the scope of the subject matter described herein. The drawings are not necessarily to scale; in some instances, various aspects of the subject matter disclosed herein may be shown exaggerated or enlarged in the drawings to facilitate an understanding of different features. In the drawings, like reference characters generally refer to like features (e.g., functionally similar and/or structurally similar elements).

To address various issues and advance the art, the entirety of this application (including the Cover Page, Title, Headings, Background, Summary, Brief Description of the Drawings, Detailed Description, Embodiments, Abstract, Figures, Appendices, and otherwise) shows, by way of illustration, various embodiments in which the embodiments may be practiced. As such, all examples and/or embodiments are deemed to be non-limiting throughout this disclosure.

It is to be understood that the logical and/or topological structure of any combination of any program components (a component collection), other components and/or any present feature sets as described in the Figures and/or throughout are not limited to a fixed operating order and/or arrangement, but rather, any disclosed order is an example and all equivalents, regardless of order, are contemplated by the disclosure.

Various concepts may be embodied as one or more methods, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments. Put differently, it is to be understood that such features may not necessarily be limited to a particular order of execution, but rather, any number of threads, processes, services, servers, and/or the like that may execute serially, asynchronously, concurrently, in parallel, simultaneously, synchronously, and/or the like in a manner consistent with the disclosure. As such, some of these features may be mutually contradictory, in that they cannot be simultaneously present in a single embodiment. Similarly, some features are applicable to one aspect of the innovations, and inapplicable to others.

The indefinite articles “a” and “an,” as used herein in the specification and in the embodiments, unless clearly indicated to the contrary, should be understood to mean “at least one.”

The phrase “and/or,” as used herein in the specification and in the embodiments, should be understood to mean “either or both” of the elements so conjoined, i.e., elements that are conjunctively present in some cases and disjunctively present in other cases. Multiple elements listed with “and/or” should be construed in the same fashion, i.e., “one or more” of the elements so conjoined. Other elements may optionally be present other than the elements specifically identified by the “and/or” clause, whether related or unrelated to those elements specifically identified. Thus, as anon-limiting example, a reference to “A and/or B”, when used in conjunction with open-ended language such as “comprising” can refer, in one embodiment, to A only (optionally including elements other than B); in another embodiment, to B only (optionally including elements other than A); in yet another embodiment, to both A and B (optionally including other elements); etc.

As used herein in the specification and in the embodiments, “of” should be understood to have the same meaning as “and/or” as defined above. For example, when separating items in a list, “of” or “and/or” shall be interpreted as being inclusive, i.e., the inclusion of at least one, but also including more than one, of a number or list of elements, and, optionally, additional unlisted items. Only terms clearly indicated to the contrary, such as “only one of” or “exactly one of,” or, when used in the embodiments, “consisting of,” will refer to the inclusion of exactly one element of a number or list of elements. In general, the term “or” as used herein shall only be interpreted as indicating exclusive alternatives (i.e., “one or the other but not both”) when preceded by terms of exclusivity, such as “either,” “one of,” “only one of,” or “exactly one of.” “Consisting essentially of,” when used in the embodiments, shall have its ordinary meaning as used in the field of patent law.

As used herein in the specification and in the embodiments, the phrase “at least one,” in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase “at least one” refers, whether related or unrelated to those elements specifically identified. Thus, as a non-limiting example, “at least one of A and B” (or, equivalently, “at least one of A or B,” or, equivalently “at least one of A and/or B”) can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the embodiments, as well as in the specification above, all transitional phrases such as “comprising,” “including,” “carrying,” “having,” “containing,” “involving,” “holding,” “composed of,” and the like are to be understood to be open-ended, i.e., to mean including but not limited to. Only the transitional phrases “consisting of” and “consisting essentially of” shall be closed or semi-closed transitional phrases, respectively, as set forth in the United States Patent Office Manual of Patent Examining Procedures, Section 2111.03.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a processor, a field programmable gate array (FPGA), and/or an application specific integrated circuit (ASIC). Software modules (executed on hardware) can include instructions stored in a memory that is operably coupled to a processor, and can be expressed in a variety of software languages (e.g., computer code), including C, C++, Java™, Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may include a single computer-readable statement or many computer-readable statements.

While specific embodiments of the present disclosure have been outlined above, many alternatives, modifications, and variations will be apparent to those skilled in the art. Accordingly, the embodiments set forth herein are intended to be illustrative, not limiting.

What is claimed is:

1. A method, comprising:

sending, to a remote compute device associated with a user, a first interaction stored in a first set of containers;

receiving, from the remote compute device, (1) a second interaction based on the first interaction and (2) data associated with the user;

analyzing, using a first stateless agent, the second interaction, a conversation history associated with the second interaction, and the data associated with the user to generate a first interaction package using a second set of containers different than the first set of containers, the conversation history stored in the first set of containers;

analyzing, using a second stateless agent different from the first stateless agent, the second interaction, the conversation history, and the data associated with the user to generate a second interaction package that is different from the first interaction package and using the second set of containers, the first interaction package including a first prompt not included in the second interaction package and the second interaction package including a second prompt not included in the first interaction package;

sending the first interaction package and the second interaction package to a large language model configured to generate a third interaction responding to the second interaction based on the first interaction package and the second interaction package; and sending a representation of the third interaction to the remote compute device that is personalized to the user.

2. The method of claim 1, further comprising:

refraining from analyzing the second interaction, the conversation history, and the data associated with the user using a third stateless agent different than the first stateless agent and the second stateless agent while the first interaction package and the second interaction package are being generated.

3. The method of claim 1, further comprising:

receiving encrypted video from the remote compute device; and decrypting the encrypted video to obtain an unencrypted video, the data associated with the user represented in the unencrypted video.

4. The method of claim 1, wherein the first stateless agent is trained using a first plurality of prompts and the second stateless agent is trained using a second plurality of prompts different from the first plurality of prompts.

5. The method of claim 1, further comprising:

determining, using a rule-based model, that the third interaction fails to satisfy at least one predetermined standard; and updating the third interaction to generate the representation of the third interaction, the representation of the third interaction (1) satisfying the at least one predetermined standard and (2) being shorter than the third interaction.

6. The method of claim 1, wherein:

the first interaction package includes at least one question derived from the second interaction, the data associated with the user, and the conversation history, the first interaction package not including an evaluation of correctness of the second interaction; and the second interaction package includes the evaluation of correctness of the second interaction, the second interaction package not including a question.

7. The method of claim 1, wherein the second stateless agent is configured to generate the second interaction package with a lower computational latency than the first stateless agent.

8. The method of claim 1, wherein the first set of containers and the second set of containers are deployed within a virtual private cloud.

9. The method of claim 1, wherein the data associated with the user is biometric data of the user.

10. A method, comprising:

sending, via a processor of a first compute device and to a second compute device, a first interaction, the second compute device associated with a user, the first interaction generated by:

extracting a reference from source material, the reference associated with contextual information within the source material, defining a template based on the reference and the contextual information, aligning the template using a first large language model and a graph database to generate an aligned template, the first large language model trained using reinforcement learning, and inputting the aligned template into a machine learning model configured to generate the first interaction;

receiving, via the processor and from the second compute device, (1) a second interaction based on the first interaction and (2) biometric data associated with the user;

analyzing, via the processor and using a stateless agent, the second interaction, a conversation history associated with the second interaction, and the biometric data to generate an interaction package;

sending, via the processor, the interaction package to a second large language model configured to generate a third interaction responding to the second interaction; and sending, via the processor, a representation of the third interaction to the second compute device.

11. The method of claim 10, wherein the interaction package is generated using a first set of containers, and the conversation history and the first interaction are stored at a second set of containers different from the first set of containers.

12. The method of claim 10, wherein the stateless agent is a first stateless agent and the interaction package is a first interaction package, the method further comprising:

analyzing, via the processor and using a second stateless agent different from the first stateless agent, the second interaction, the conversation history, and the biometric data to generate a second interaction package that is different from the first interaction package; and sending, via the processor, the second interaction package to the second large language model, the second large language model further configured to generate the third interaction based on the second interaction package.

13. The method of claim 10, wherein the stateless agent is a first stateless agent and the interaction package is a first interaction package, the method further comprising:

analyzing, via the processor, using a second stateless agent different from the first stateless agent, and while the first stateless agent is analyzing the second interaction, the conversation history, and the biometric data to generate the first interaction package, the second interaction, the conversation history, and the biometric data to generate a second interaction package that is different from the first interaction package; and sending, via the processor, the second interaction package to the second large language model, the second large language model further configured to generate the third interaction based on the second interaction package.

14. The method of claim 10, further comprising:

analyzing, via the processor, at least one of the second interaction or the biometric data to identify the stateless agent from a plurality of stateless agents, the analyzing of the second interaction, the conversation history, and the biometric data to generate the interaction package occurring (1) in response to identifying the stateless agent from the plurality of stateless agents and (2) without using remaining agents from the plurality of stateless agents.

15. The method of claim 10, further comprising:

receiving a profile representing the user, the profile indicating at least one of an age of the user or a geography of the user; and analyzing, via the processor, the profile and at least one of the second interaction or the biometric data to identify the stateless agent from a plurality of stateless agents, the analyzing of the second interaction, the conversation history, and the biometric data to generate the interaction package occurring (1) in response to identifying the stateless agent from the plurality of stateless agents and (2) without using remaining agents from the plurality of stateless agents.

16. The method of claim 10, wherein generating the first interaction further includes:

validating the first interaction using a process reward model, the first interaction sent to the second compute device in response to validating the first interaction.

17. The method of claim 10, wherein analyzing the second interaction, the conversation history, and the biometric data to generate the interaction package includes:

determining a state of the user based on the biometric data, the state indicating a distraction level of the user.

18. The method of claim 10, wherein the stateless agent is a first stateless agent and the interaction package is a first interaction package, the method further comprising:

receiving, via the processor and from the second compute device, a fourth interaction responding to the representation of the third interaction;

determining, via the processor, that the fourth interaction fails to satisfy a criterion;

analyzing, via the processor, in response to determining that the fourth interaction fails to satisfy the criterion, and using a second stateless agent different from the first stateless agent, the conversation history and the fourth interaction to generate a second interaction package;

sending, via the processor, the second interaction package to the second large language model to generate a fifth interaction responding to the fourth interaction; and sending, via the processor, a representation of the fifth interaction to the second compute device.

19. A non-transitory, processor-readable medium comprising instructions that, when executed by one or more processors, cause the one or more processors to:

send, to a remote compute device associated with a user, a first interaction stored in a first set of containers;

receive, from the remote compute device, a second interaction based on the first interaction;

analyze, using a first stateless agent, the second interaction and a conversation history associated with the second interaction to generate a first interaction package using a second set of containers, the conversation history stored in the first set of containers;

analyze, using a second stateless agent different from the first stateless agent, the second interaction and the conversation history to generate a second interaction package that is different from the first interaction package and using the second set of containers;

send the first interaction package and the second interaction package to a model configured to generate a third interaction responding to the second interaction based on the first interaction package and the second interaction package; and send a representation of the third interaction to the remote compute device.

20. The non-transitory, processor-readable medium of claim 19, wherein the first interaction is generated by:

extracting a reference from source material, the reference associated with contextual information within the source material, the reference being an image;

transforming the reference into a template;

aligning the template using a large language model and a graph database to generate an aligned template, the large language model trained using reinforcement learning;

embedding the aligned template to generate an embedding;

assigning the embedding to a cluster from a plurality of clusters; and inputting the aligned template, an indication of the cluster, and the contextual information into a machine learning model to generate the first interaction.

21. The non-transitory, processor-readable medium of claim 19, wherein the first interaction package includes a prompt to assist the user with the first interaction without providing an answer to the first interaction, and the second interaction package includes a prompt to provide the answer to the first interaction if the second interaction differs from the answer.

* * * * *